(12) United States Patent
Tanaka et al.

(10) Patent No.: US 10,010,242 B2
(45) Date of Patent: Jul. 3, 2018

(54) ENDOSCOPE

(71) Applicant: FUJIFILM Corporation, Tokyo (JP)

(72) Inventors: Toshizumi Tanaka, Kanagawa (JP);
Masayuki Iwasaka, Kanagawa (JP);
Teruyuki Emura, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 72 days.

(21) Appl. No.: 15/073,663

(22) Filed: Mar. 18, 2016

(65) Prior Publication Data

US 2016/0270637 A1 Sep. 22, 2016

(30) Foreign Application Priority Data

Mar. 20, 2015 (JP) ................. 2015-058349

(51) Int. Cl.
*A61B 1/00* (2006.01)
(52) U.S. Cl.
CPC ......... *A61B 1/00098* (2013.01); *A61B 1/0011* (2013.01); *A61B 1/00137* (2013.01)
(58) Field of Classification Search
CPC ........................... A61B 1/0098; A61B 1/00101
USPC ................. 600/106, 107, 127, 133
See application file for complete search history.

(56) References Cited

U.S. PATENT DOCUMENTS

| 5,562,600 | A | * | 10/1996 | Matsuno | ............... | A61B 1/018 600/107 |
| 5,730,701 | A | * | 3/1998 | Furukawa | ............. | A61B 1/0008 600/121 |
| 8,246,534 | B2 | * | 8/2012 | Yamaya | ............ | A61B 1/00098 600/104 |
| 2004/0082836 | A1 | | 4/2004 | Hino | | |
| 2007/0270638 | A1 | * | 11/2007 | Kitano | ............... | A61B 1/00098 600/104 |

FOREIGN PATENT DOCUMENTS

JP 2004-141315 5/2004

* cited by examiner

*Primary Examiner* — Rynae Boler
(74) *Attorney, Agent, or Firm* — JCIPRNET

(57) ABSTRACT

There is provided an endoscope which can clean a distal end portion promptly and easily. An elevator housed in an elevator housing space of a distal end portion body is coupled with an erecting lever of an erecting lever housing chamber through a rotating shaft. A first shaft portion which is engaged with an engagement hole of the elevator and a second shaft portion which is provided on the distal end side of the first shaft portion and is loosely fitted to an engagement hole of the elevator are provided in the rotating shaft. The elevator is avoided from the elevator housing slit by loosely fitting the engagement hole of the elevator to the second shaft portion at cleaning.

7 Claims, 13 Drawing Sheets

ENDOSCOPE

CROSS-REFERENCE TO RELATED APPLICATIONS

The present application claims priority under 35 U.S.C. § 119 to Japanese Patent Application No. 2015-058349, filed on Mar. 20, 2015. Each of the above application(s) is hereby expressly incorporated by reference, in their entirety, into the present application.

BACKGROUND OF THE INVENTION

Field of the Invention

The present invention relates to an endoscope, and specifically relates to an endoscope including an elevator.

Description of the Related Art

Regarding an endoscope, various treatment tools are inserted into a treatment-tool entry port provided on an operation portion and they are led out of the treatment-tool exit port opened in the distal end portion and used for treatment. The treatment tools such as a guide wire, a contrast medium tube and the like are used for a duodenoscopy, puncture needles for an ultrasonic endoscope, and forceps, snares and the like for a direct-viewing endoscope or a side-viewing endoscope, for example. These treatment tools need to change a derivation direction at the distal end portion in order to treat a desired position in a subject, and thus, a treatment-tool elevating mechanism (forceps elevator, hereinafter referred to as an "elevator") is provided on the distal end portion.

As such the treatment-tool elevating mechanisms, a mechanism in which a wire is attached to the elevator and extended to a proximal end side of the endoscope, is known. In the mechanism, the elevator is rotated around a rotating shaft by pushing and pulling operation of the wire with an operation lever provided on the operation portion so as to change a position of the elevator between an erecting position and a reclining position. Moreover, a mechanism (lever type) in which the rotating shaft of the elevator is coupled with a housed lever through a partition wall, and the wire is attached to the lever is also known. In the mechanism, the elevator is rotated around the rotating shaft by means of the pushing and pulling operation of the wire with the operation lever provided on the operation portion so as to change the position of the elevator between the erecting position and the reclining position.

The distal end portion provided with such a treatment-tool elevating mechanism has a complicated shape and structure and thus, improvement of cleaning performances such as wraparound of a disinfectant, insertion of a cleaning brush (reachability of a tip end of the brush) or drainage and ease of a cleaning work are in demand. Conventionally, an endoscope having a detachable cap on the distal end portion is known (see Japanese Patent Laid-Open No. 2004-141315, for example). In this type of endoscope, the cap is removed after treatment, and then the distal end portion is cleaned.

SUMMARY OF THE INVENTION

However, in an endoscope in the related art as described in Japanese Patent Laid-Open No. 2004-141315, in addition to the fact that a distal end portion itself is originally small, exposed portions are small because an elevator is housed in an elevator housing slit. Moreover, the gap between the elevator and the elevator housing slit is narrow, and therefore it takes time for cleaning using a brush or the like.

The present invention has been made in view of such circumstances, and it is an object to provide an endoscope which can clean a distal end portion promptly and easily.

To attain the above-mentioned object, an endoscope according to one aspect of the present invention includes: an insertion portion which includes a distal end and a proximal end; an operation portion which is provided on a proximal end side of the insertion portion and includes an operating member and; a distal end portion body which is provided on a distal end side of the insertion portion, and has a front surface being a surface in a longitudinal direction of the insertion portion, an upper surface being a surface in a direction in which a treatment tool is led out with respect to the longitudinal direction and a lower surface being a surface on a side opposite to the upper surface with respect to the longitudinal direction; an elevator which is rotatably provided in the distal end portion body; a rotating shaft provided with an axis and configured to rotate the elevator around the axis, the rotating shaft including a first shaft portion and a second shaft portion connected with one end of the first shaft portion, wherein a cross section vertical to a direction of the axis of the rotating shaft in the first shaft portion has a non-circular shape, and a cross-sectional area of a cross section vertical to the direction of the axis in the second shaft portion is smaller than a cross-sectional area of the cross section of the first shaft portion; a rotating shaft receiving portion provided in the elevator, the rotating shaft receiving portion including a rotating shaft receiving region which is engaged with the first shaft portion in a relatively unrotatable manner and is loosely fitted to the second shaft portion in a relatively rotatable manner; an elevator erecting mechanism configured to rotate the rotating shaft; an operating wire which includes a proximal-end-side coupling portion coupled with the operating member and a distal-end-side coupling portion coupled with the elevator erecting mechanism, the operating wire being configured to rotate the rotating shaft to recline or erect the elevator when the operating wire is pushed or pulled by operation of the operating member; an elevator housing slit which is provided in the distal end portion body and forms a space portion to house the elevator, the elevator housing slit including an opening on a side of the upper surface, on a side of the lower surface and on a side of the front surface; and a cap which is detachably provided in the distal end portion body, the cap including an opening window which opens a part of the opening on the side of the upper surface, and a partition wall portion which closes a part of the opening portion on the side of the lower surface in a state in which the cap is attached to the distal end portion body, wherein: the distal end portion body includes a position restricting portion which is configured to restrict a relative position of the rotating shaft with respect to the rotating shaft receiving region of the rotating shaft receiving portion; and when the elevator is located in a first position in a rotation direction, the position restricting portion restricts the relative position of the rotating shaft with respect to the rotating shaft receiving region of the rotating shaft receiving portion to the first shaft portion, and, when the elevator is located in a second position in the rotation direction, the position restricting portion allows the relative position of the rotating shaft with respect to the rotating shaft receiving region of the rotating shaft receiving portion to move from the first shaft portion to the second shaft portion.

According to the aspect, since it is possible to retreat most of the elevator to the outside of the elevator housing slit and clean the elevator and the elevator housing slit, it is possible to perform cleaning easily and promptly.

In an endoscope according to another aspect of the present invention, the first position is a position in which a whole of the elevator is housed inside the elevator housing slit.

In the endoscope according to another aspect of the present invention, the second position is a position in which at least a part of the elevator is exposed to the outside of the elevator housing slit.

In an endoscope according to another aspect of the present invention, the second position is a position in which at least a part of the elevator is exposed from the part of the opening on the side of the lower surface to the outside.

In an endoscope according to another aspect of the present invention, the second position is a position in which at least a part of the elevator is exposed from the part of the opening on the side of the upper surface to the outside.

In an endoscope according to another aspect of the present invention, the rotating shaft is configured in a cantilever shape in which one end of the rotating shaft is a fixed end fixed to the elevator erecting mechanism and another end is a free end.

In an endoscope according to another aspect of the present invention, the elevator erecting mechanism includes an elevator erecting lever coupled with the rotating shaft; the distal-end-side coupling portion of the operating wire is coupled with the elevator erecting lever; and, when the operating wire is pushed or pulled by operation of the operating member, the operating wire rotates the rotating shaft through the elevator erecting lever to recline or erect the elevator.

According to the present invention, it is possible to clean a distal end portion promptly and easily.

DETAILED DESCRIPTION OF THE EMBODIMENTS

In the following, preferable embodiments of the present invention are described in detail with reference to the accompanying drawings.

Figure 1:
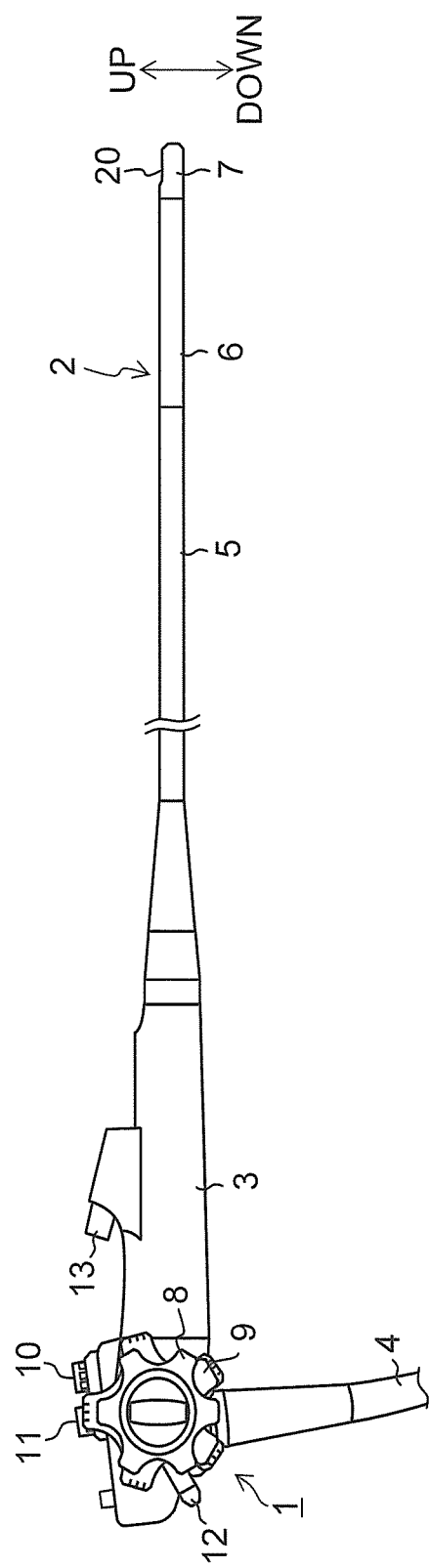
FIG. 1 is a configuration diagram illustrating an endoscope 1 according to the present invention.

FIG. 1 is a configuration diagram illustrating the endoscope 1 according to the present invention.

The endoscope 1 in this figure includes an insertion portion 2 which is to be inserted in a patient's body, an operation portion 3 which is continuously provided in the proximal end surface of the insertion portion 2 and is used to hold the endoscope 1 and operate the insertion portion 2, and a universal cord 4 which connects the endoscope 1 with system configuration equipment such as an unillustrated light source device and processor device, and so on.

The insertion portion 2 is formed with a flexible portion 5, a bending portion 6 and a distal end portion 7 which are provided in this order from the proximal end to the distal end. The flexible portion 5 has flexibility and bends in an arbitrary direction along an insertion path of the insertion portion 2. The bending portion 6 bends in each of the upper, lower, right and left directions by operation of each of angle knobs 8 and 9 of the operation portion 3. The distal end portion 7 includes an observing portion that takes an image of an observed site in a body and sends the taken image to a processor device connected by the universal cord 4 as an observation image (endoscope image), and an illuminating portion that emits illumination light, which is propagated from a light source device connected by the universal cord 4 through a light guide inside the endoscope 1, to the observed site, and so on.

Figure 2:
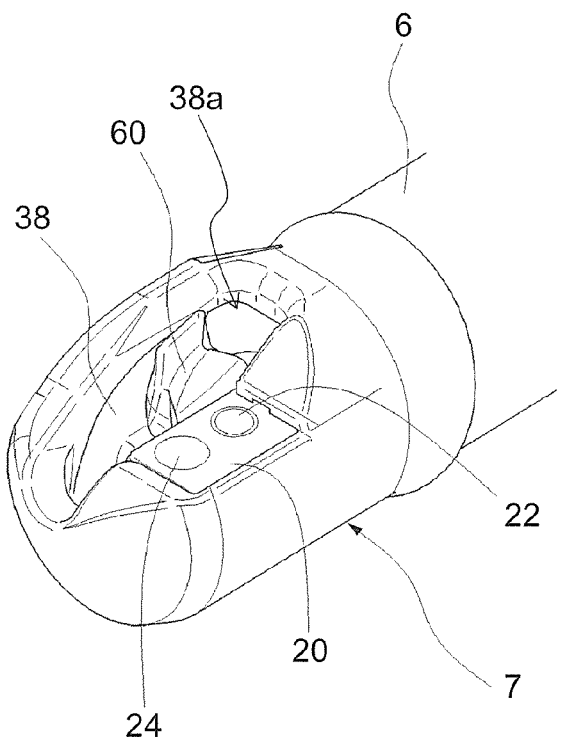
FIG. 2 is an expanded perspective view that illustrates a distal end portion.

FIG. 2 is an expanded perspective view that illustrates the distal end portion 7. The endoscope 1 of the present embodiment is a side-viewing endoscope used as a duodenoscope, for example, and the distal end portion 7 in this figure shows a configuration in the side-viewing endoscope.

As illustrated in the figure, a flat surface 20 which is substantially parallel to a longitudinal axis that is the axis of the insertion portion 2 is provided in the distal end portion 7, and the observation window 22 and an illumination window 24 are provided in the flat surface 20. Here, in the following, in a case where the longitudinal axis is merely referred to, the longitudinal axis of the insertion portion 2 is shown.

The observation window 22 is a component of the observing portion which obtains an image of an observed site that exists on the lateral side (radial direction) with respect to the longitudinal axis, and receives object light from an observed portion on the lateral side in an optical system (an imaging lens or the like) and an imaging device that are other components of the observing portion. The illumination window 24 is a component of the illuminating portion mounted to the distal end portion 7, and emits illumination light to the observed site from a light emitting portion which is another component of the illuminating portion, that is, from the light emitting portion provided in a termination portion of the light guide which propagates light from a light source device.

Here, as for the distal end portion 7, a position on the distal end side which is a longitudinal axis direction is the front side (distal end side), a position on the opposite side thereof is the rear side (proximal end side), a position which is in a direction vertical to the flat surface 20 and is opposed to the flat surface 20 is the upper side, the opposite side thereof is the lower side (see FIG. 1), and the left side and the right side are positions in a direction decided by the relationship between the front and rear position and the upper and lower position.

Moreover, an elevator housing slit 38 is provided on the right side of the flat surface 20 in the distal end portion 7, and an elevator 60 is provided in the elevator housing slit 38. The elevator housing slit 38 communicates with a treatment tool introduction port 13 (see FIG. 1) of the operation portion 3 through a treatment tool insertion channel inserted in the insertion portion 2, and a treatment tool inserted from the treatment tool introduction port 13 is led to the elevator housing slit 38.

The elevator 60 bends the travelling direction of the treatment tool led to the elevator housing slit 38, guides it to a direction toward the opening portion (opening) 38a (which may be referred to as "treatment entry port 38a") on the upper surface side of the elevator housing slit 38, and leads out the treatment tool from the treatment entry port 38a.

Moreover, the elevator 60 performs erecting and reclining operation (rotates) in a direction for erecting (erecting direction) or a direction for falling (falling direction) by operation of an erecting operation lever 12 (see FIG. 1) of the operation portion 3, and changes the delivery direction (delivery angle) of the treatment tool from the treatment entry port 38a.

Here, an unillustrated air-supply and water-supply nozzle which can switch between air supply and water supply to the observation window 22 by operation of an air-supply and water-supply button 10 (see FIG. 1) of the operation portion 3 is provided near the observation window 22 of the flat surface 20. Moreover, a suction channel is connected with the treatment tool insertion channel in the insertion portion 2, and suction from the elevator housing slit 38 is performed by operation of a suction button 11 of the operation portion 3 (see FIG. 1).

Subsequently, a configuration related to the drive mechanism of the elevator 60 in the distal end portion 7 is described in detail.

Figure 3:
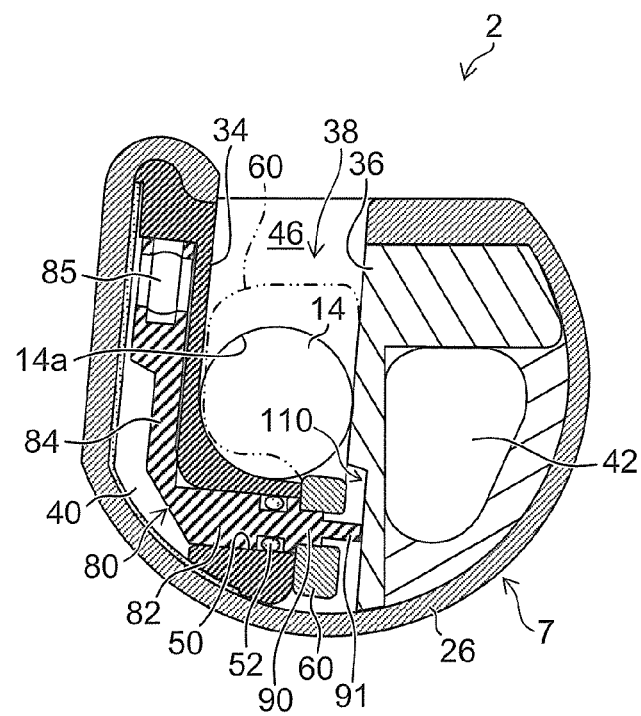
FIG. 3 is a cross-sectional view of a distal end portion.
Figure 4:
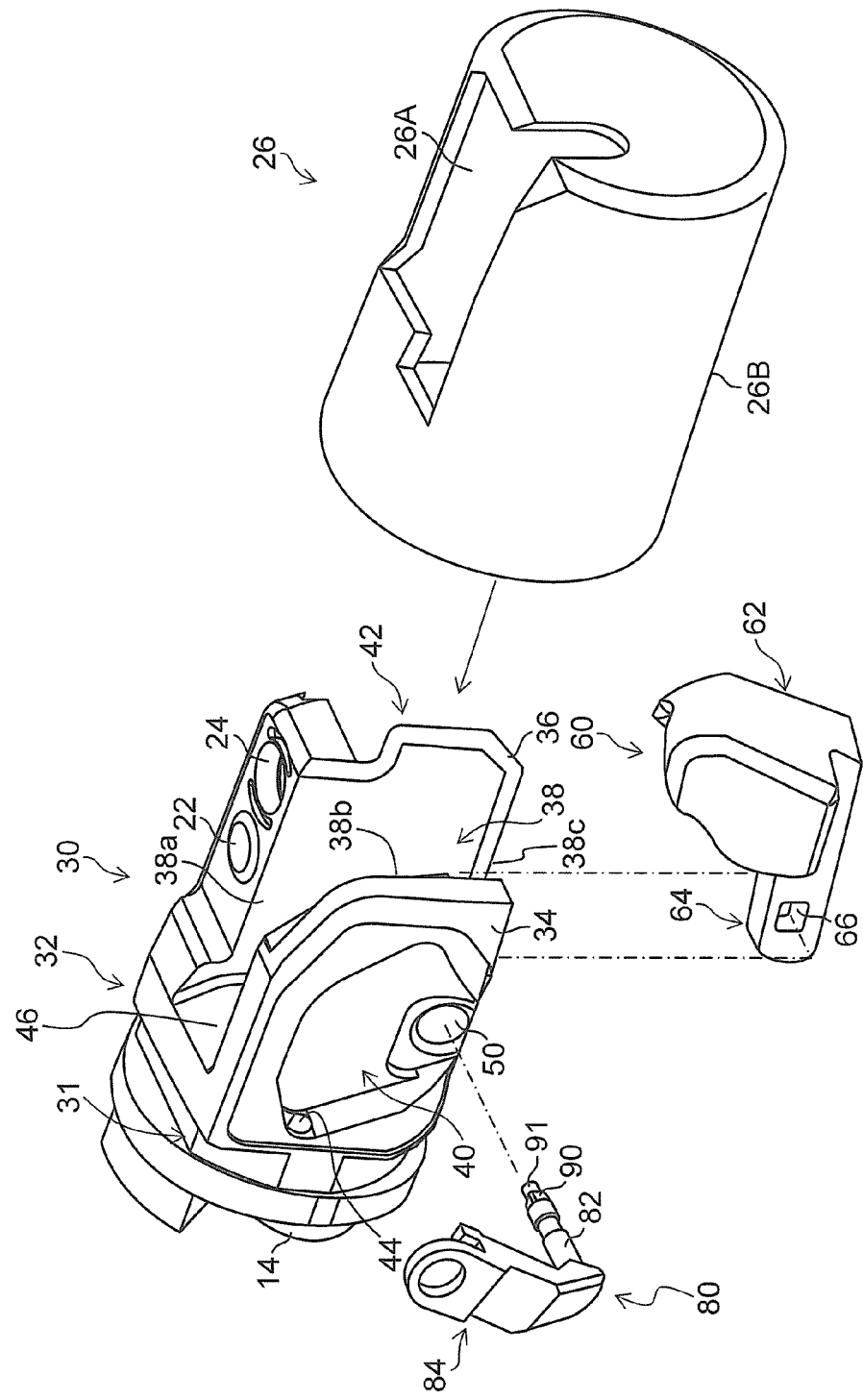
FIG. 4 is an exploded perspective view of a distal end portion.

FIG. 3 is a cross-sectional view of the distal end portion 7 vertical to the longitudinal axis, and FIG. 4 is an exploded perspective view of the distal end portion 7.

As illustrated in these figures, the distal end portion 7 includes a distal end portion body 30 (see FIG. 4) which divides the inside of the distal end portion 7 into a plurality of regions and to which various components are integrally assembled, and is covered with a cap 26 which is detachable for the outer peripheral portion of the distal end portion body 30.

The cap 26 is made of an elastic material such as elastic rubber and formed in a shape based on a cylindrical shape in which the distal end side is closed, and includes: an opening window 26A which opens the above-mentioned flat surface 20, the whole of the opening portion 38a (treatment entry port 38a) on the upper surface side of the elevator housing slit 38 and a part on the upper side of an opening portion 38b on the front surface side; and a partition wall portion 26B which closes the whole of an opening portion 38c on the lower surface side of the elevator housing slit 38 and a part on the lower side of the opening portion 38b on the front surface side.

Moreover, an engagement portion (not illustrated) which annularly projects toward the inside in the radial direction is formed in the proximal end of the cap 26, and the cap 26 is attached to the distal end portion body 30 by engaging the engagement portion with a groove 31 formed in the outer peripheral portion of the distal end portion body 30. Moreover, the cap 26 is detached at the time of cleaning as described later.

The distal end portion body 30 is formed with a rigid member such as a metal material having corrosion resistance, and includes a columnar proximal end portion 32 on the proximal end side and a pair of right and left side wall portions 34 and 36 which are extended from the proximal end portion 32 to the distal end side and face each other. By this means, in the distal end portion 7, the elevator housing slit 38 that is a space portion which houses the elevator 60 is formed between the right side wall portion 34 and the left side wall portion 36, an erecting lever housing chamber 40 that is a space portion which houses an erecting lever 84 described below is formed on the right side from the side wall portion 34, and an optical system housing chamber 42 that is a space portion which houses components (not illustrated) of the above-mentioned observing portion and illuminating portion is formed on the left side from the side wall portion 36. Here, the erecting lever housing chamber 40 and the optical system housing chamber 42 are covered with an unillustrated protective plate in FIG. 4 to hold airtightness.

In a state in which the cap 26 is detached from the distal end portion body 30 as illustrated in FIG. 4, the elevator housing slit 38 includes an opening portion on the upper surface side as the opening portion 38a (treatment entry port 38a), an opening portion on the front surface side as the opening portion 38b and an opening portion on the lower surface side as the opening portion 38c. And the elevator housing slit 38 extends and opens from the upper surface to the lower surface through the front surface since those opening portions 38a, 38b and 38c are continuously provided.

Moreover, a rear wall portion 46 formed with the proximal end portion 32 of the distal end portion body 30 is disposed on the proximal end side of the elevator housing slit 38, and an opening portion 14a that is a conduit end portion of a treatment tool insertion channel 14 is disposed in the rear wall portion 46 as illustrated in FIG. 3.

The elevator 60 whose entire image is illustrated in FIG. 4 is rotatably installed in this elevator housing slit 38. Here, the configuration of the elevator 60 is described later.

A holding hole 50 that penetrates from the erecting lever housing chamber 40 to the elevator housing slit 38 as illustrated in FIGS. 3 and 4 is formed near the lower end of the side wall portion 34 disposed on the right side of the elevator housing slit 38, and a rotating shaft 82 is rotatably supported to the holding hole 50.

Here, in the present embodiment, as illustrated in FIG. 4, the rotating shaft 82 is integrally formed with the erecting lever 84, is extended from the proximal end of the erecting lever 84 that extends in a tabular shape, and is formed in a cantilever shape such that one end of the rotating shaft 82 is a fixed end which is fixed to the erecting lever 84 that is an elevator erecting mechanism and the other end is a free end. A member including this rotating shaft 82 and the erecting lever 84 that extends in a direction substantially vertical to the axis of the rotating shaft 82 is a driving member 80, but the rotating shaft 82 and the erecting lever 84 may be formed separately from each other.

Moreover, a seal member 52 is disposed between the rotating shaft 82 and the holding hole 50 as illustrated in FIG. 3, and the gas and the liquid are prevented from mutually entering between the elevator housing slit 38 and the erecting lever housing chamber 40.

An end portion (first shaft portion 90) which projects to an elevator housing slit 38 of this rotating shaft 82 is coupled with an elevator 60 as described later.

As illustrated in FIG. 4, a fan-shaped space portion centering on the holding hole 50 is formed on the right side of the side wall portion 34 as the erecting lever housing chamber 40. In this erecting lever housing chamber 40, the rotating shaft 82 of the driving member 80 is inserted in the holding hole 50 and the erecting lever 84 of the driving member 80 is housed.

Figure 5:
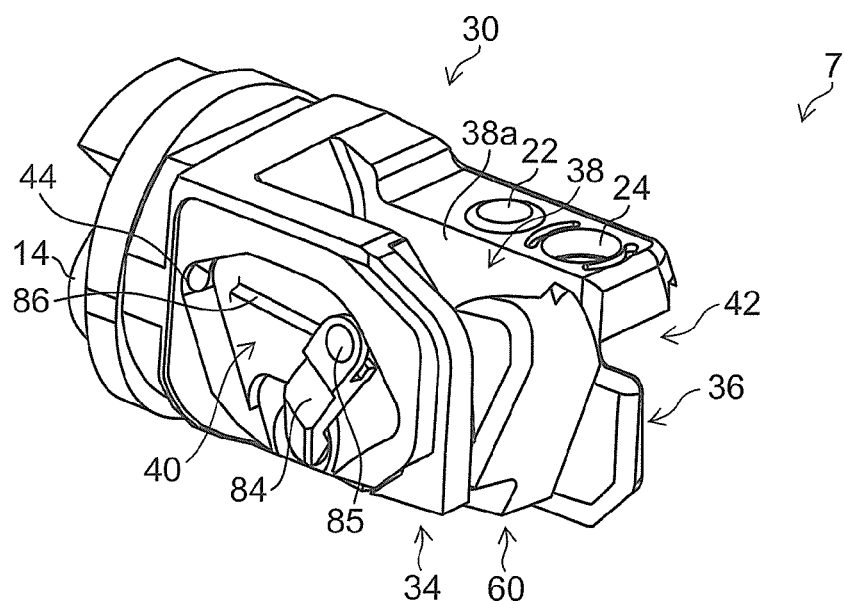
FIG. 5 is a perspective view illustrating a state in which an elevator and a driving member are assembled to a distal end portion body.

FIG. 5 is a perspective view illustrating a state in which the elevator 60 and the driving member 80 are assembled to the distal end portion body 30. Here, a protective plate that covers the erecting lever housing chamber 40 is omitted.

As illustrated in the figure, the distal end portion of an operating wire 86 is coupled with the distal end of the erecting lever 84 through a coupling tool 85. The operating wire 86 is inserted in the insertion portion 2 from a wire insertion hole 44 opened to the wall surface of the erecting lever housing chamber 40 and is coupled with the erecting operation lever 12 of the operation portion 3.

By this means, the operating wire 86 is pushed or pulled by operation of the erecting operation lever 12, and the erecting lever 84 rotates together with the rotating shaft 82. Further, the elevator 60 rotates by the rotation of the rotating shaft 82, and the elevator 60 performs erecting and reclining operation. Here, an elevator erecting mechanism that rotates the rotating shaft 82 is not limited to the one of the present embodiment which pushes or pulls the erecting lever 84 by the operating wire 86.

Next, a coupling mechanism between the elevator 60 and the rotating shaft 82, and so on, are described.

Figure 6:
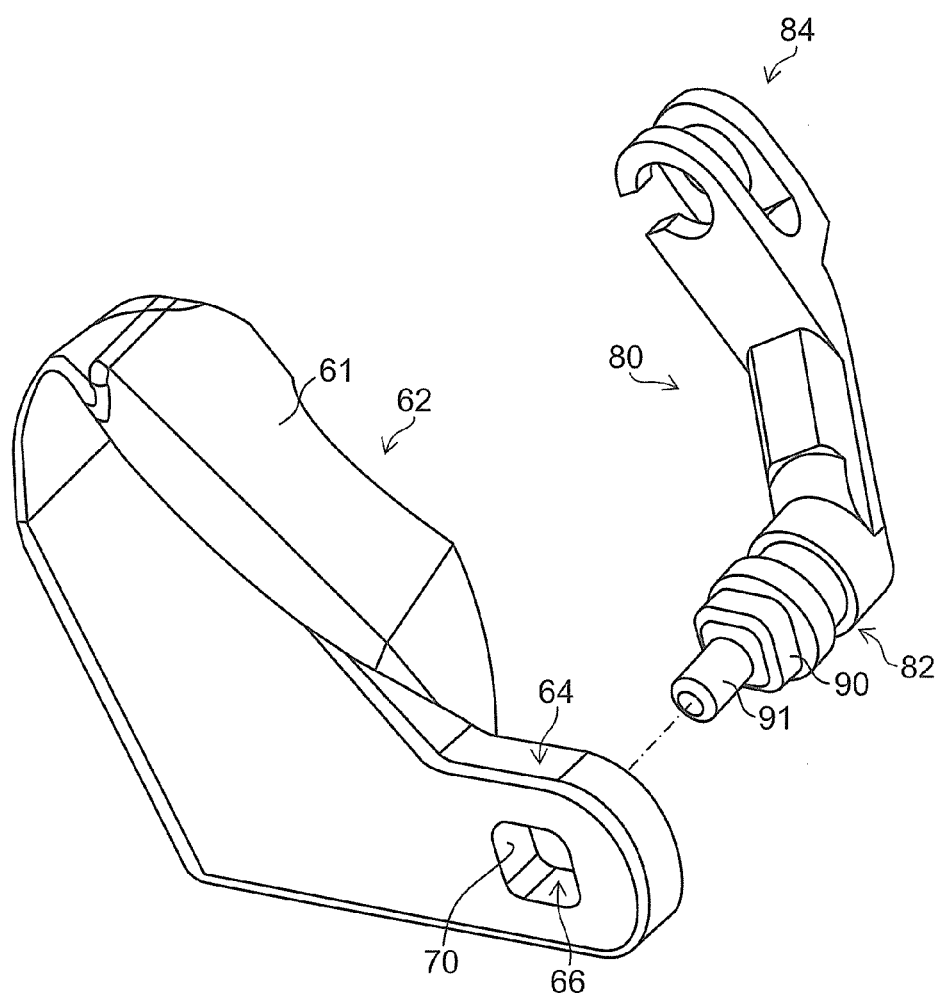
FIG. 6 is a perspective view illustrating an elevator and a driving member.

FIG. 6 is a perspective view illustrating only the elevator 60 and the driving member 80.

As illustrated in the figure and FIG. 4, the first shaft portion 90 whose cross-sectional surface vertical to the shaft direction is substantially square, as one mode of a non-circular shape, is projected on the distal end of the rotating shaft 82 of the driving member 80. In addition, a second shaft portion 91 whose cross-sectional area of a cross section vertical to the shaft direction is smaller than the first shaft portion 90 is projected on the front end side of the first shaft portion 90.

As illustrated in FIG. 3, only portions of these first shaft portion 90 and second shaft portion 91 project from the holding hole 50 of the side wall portion 34 to the elevator housing slit 38, and the distal ends thereof are disposed closely to (near) the side wall portion 36.

Figure 9:
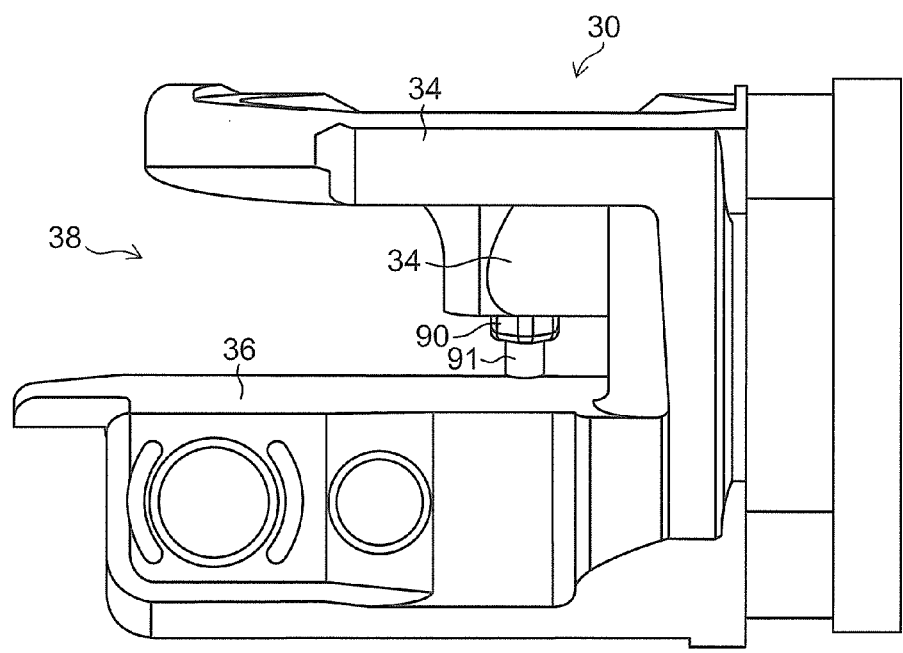
FIG. 9 is a plan view illustrating the distal end portion body from the upper side.

Moreover, FIG. 9 is a plan view illustrating the distal end portion body 30 from the upper side, which is illustration in which the elevator 60 is omitted. As understood from this figure and FIG. 3, a portion in which the holding hole 50 of the side wall portion 34 is formed projects in a direction approaching the side wall portion 36 so as to narrow a gap between the side wall portion 34 and the side wall portion 36.

Meanwhile, the elevator 60 includes: an elevator body 62 having a guide surface 61 which guides a treatment tool led out from the opening portion 14a of the treatment tool insertion channel 14 to the direction of the treatment entry port 38a; and a coupling portion 64 which projects to the proximal end side from the elevator body 62 and is formed with a narrower width than the elevator body 62.

A rotating shaft receiving portion 66 in which the first shaft portion 90 and the second shaft portion 91 of the rotating shaft 82 are inserted is provided in the coupling portion 64. The rotating shaft receiving portion 66 includes a rotating shaft receiving region 70 which is engaged with the first shaft portion 90 of the rotating shaft 82 in a relativity unrotatable manner and is loosely fitted to the second shaft portion 91 of the rotating shaft 82 in a relatively rotatable manner.

Figure 7:
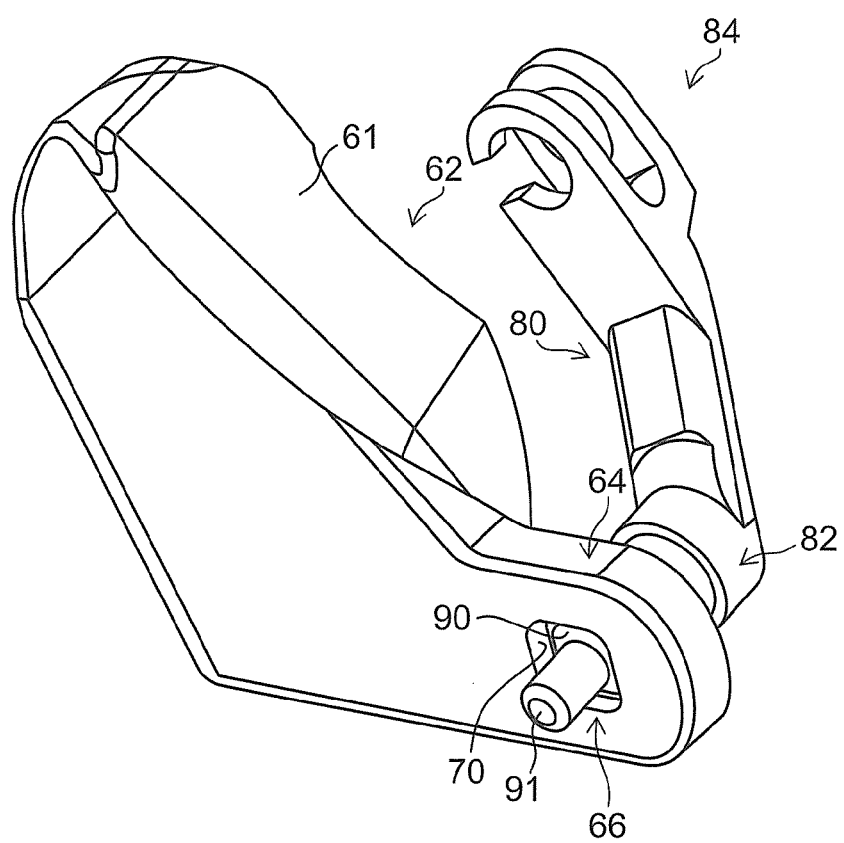
FIG. 7 is a perspective view illustrating the elevator and the driving member.

That is, the rotating shaft receiving region 70 is an engagement hole which substantially matches the shape and size of the first shaft portion 90 of the rotating shaft 82. When this rotating shaft receiving region 70 is engaged with the first shaft portion 90 of the rotating shaft 82 as illustrated in FIG. 7, the rotating shaft 82 and the elevator 60 are coupled with each other in a synchronously rotatable manner.

When the endoscope 1 is normally used for operation, it is set to this state.

Figure 8:
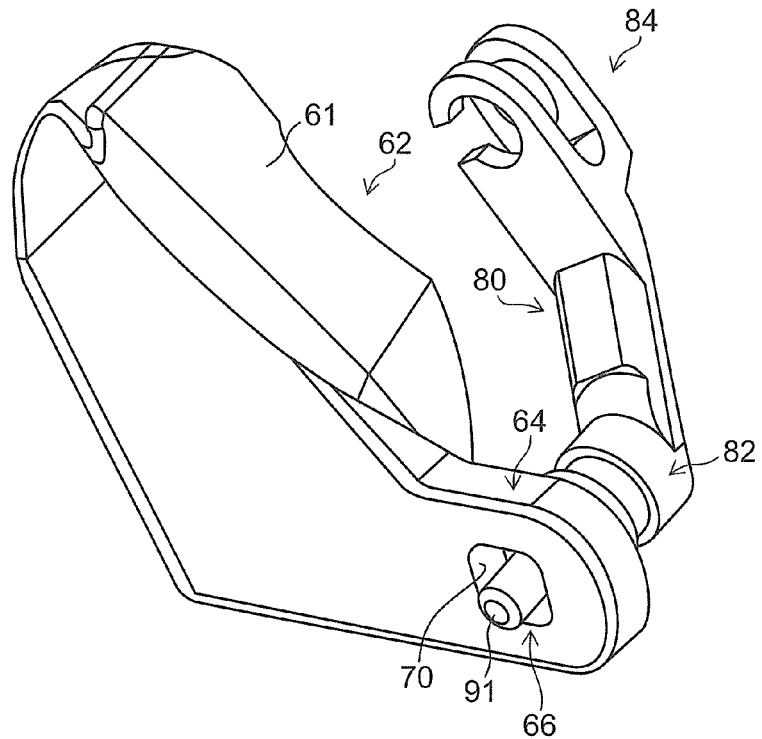
FIG. 8 is a perspective view illustrating the elevator and the driving member.

Meanwhile, the rotating shaft receiving region 70 is a big hole compared to the second shaft portion 91 of the rotating shaft 82, and, by moving the rotating shaft receiving region 70 from a position where the rotating shaft receiving region 70 engages with the first shaft portion 90 toward the distal end side of the rotating shaft 82, the rotating shaft receiving region 70 enters a state in which the rotating shaft receiving region 70 is loosely fitted to the second shaft portion 91 of the rotating shaft 82 as illustrated in FIG. 8.

Therefore, the coupling between the rotating shaft 82 and the elevator 60 is released. At this time, by directly applying a force to the elevator 60, the elevator 60 enters a state in which only the elevator 60 can be rotated around the axis of the rotating shaft 82 without the rotation of the erecting lever 84 and the rotating shaft 82.

By setting this state when the endoscope 1 is cleaned, it is possible to retreat most of the elevator 60 from the elevator housing slit 38, clean the inside of the elevator housing slit 38 and the elevator 60. Thus, cleaning of the distal end portion 7 can be performed easily and promptly.

Moreover, the elevator 60 does not move to a position in which the rotating shaft receiving region 70 loosely fits to the second shaft portion 91 of the rotating shaft 82, such that the elevator 60 and the rotating shaft 82 are in a state in which they are always coupled with each other when the endoscope 1 is normally used for operation.

Figure 10:
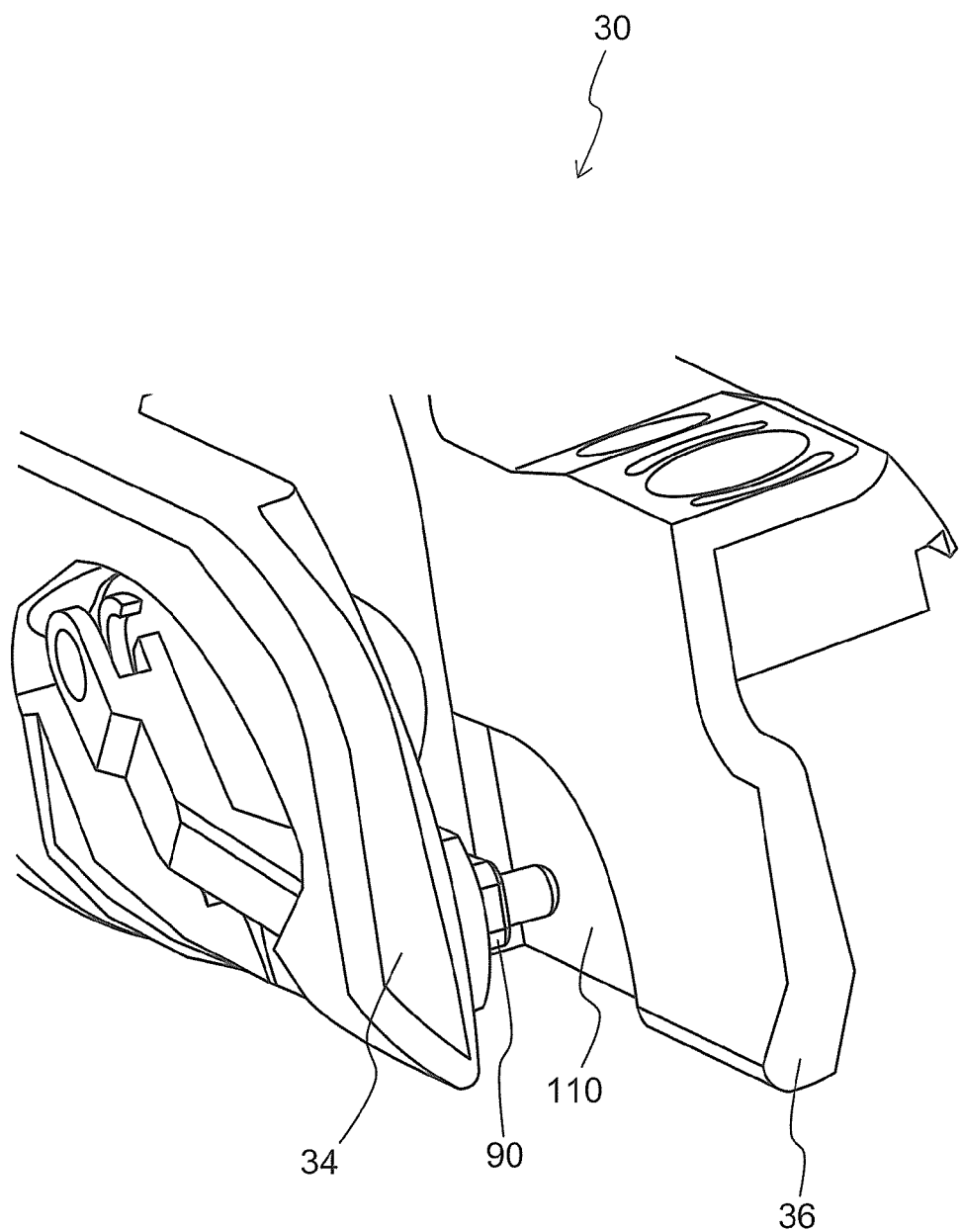
FIG. 10 is a diagram illustrating a concave portion formed in a side wall portion of the distal end portion body.

That is, a concave portion 110 is formed in the side wall portion 36 as illustrated in FIG. 10 (see FIG. 3 also). If even at least a part of the elevator 60 overlaps with the opposing range of a region other than the concave portion 110 of the side wall portion 36, the movement of the axial direction of the rotating shaft 82 is restricted, and the elevator 60 is maintained in a state in which the rotating shaft receiving region 70 is engaged with the first shaft portion 90 of the rotating shaft 82.

Further, when the endoscope 1 is normally used for operation, the rotation range of the elevator 60 is limited to a range subjected to such the restriction. Therefore, when the endoscope 1 is normally used for operation, the elevator 60 and the rotating shaft 82 are maintained in a state in which they are always coupled with each other.

The function of the distal end portion 7 mentioned above is described.

Figure 11A:
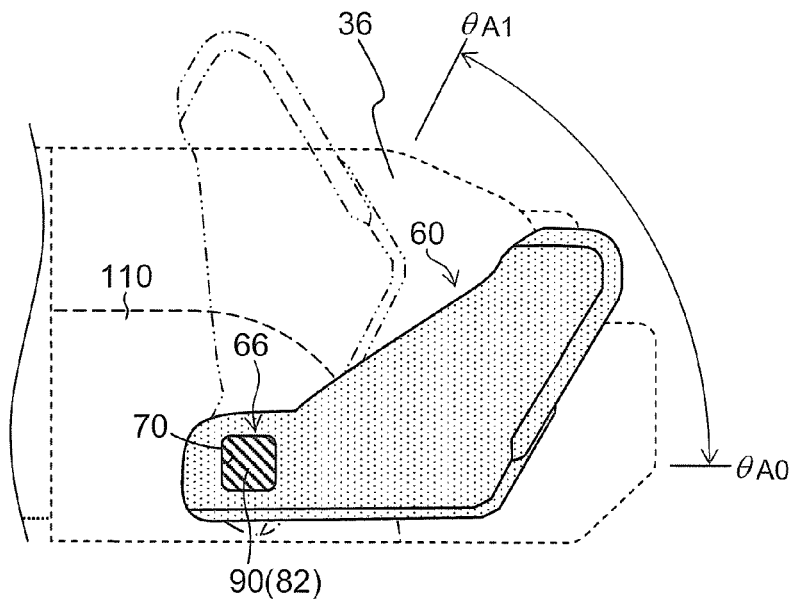
FIGS. 11A and 11B are explanatory drawings used to describe the function of the distal end portion.
Figure 11B:
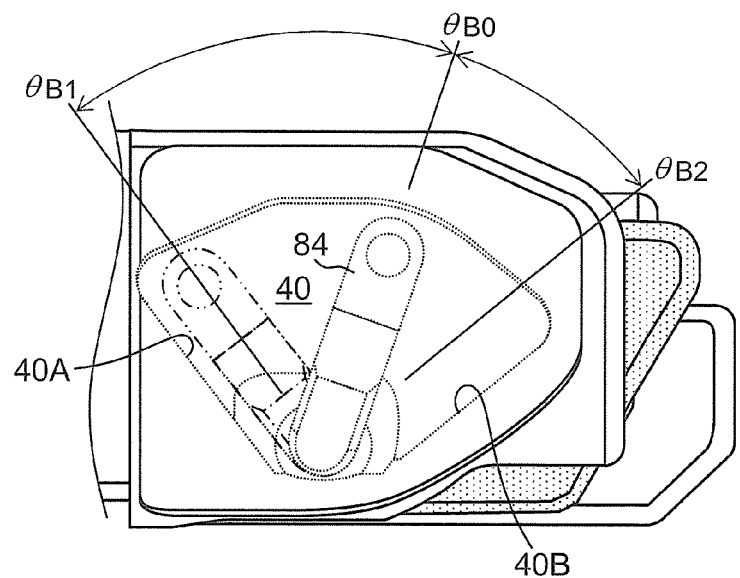
Figure 12A:
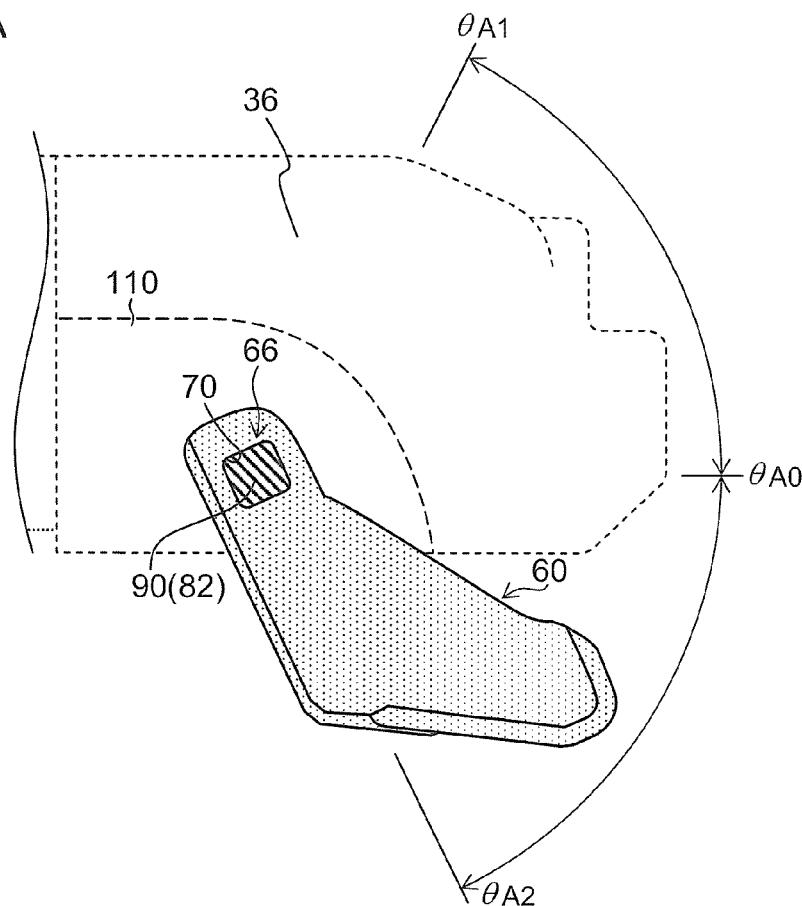
FIGS. 12A and 12B are explanatory drawings used to describe the function of the distal end portion.
Figure 12B:
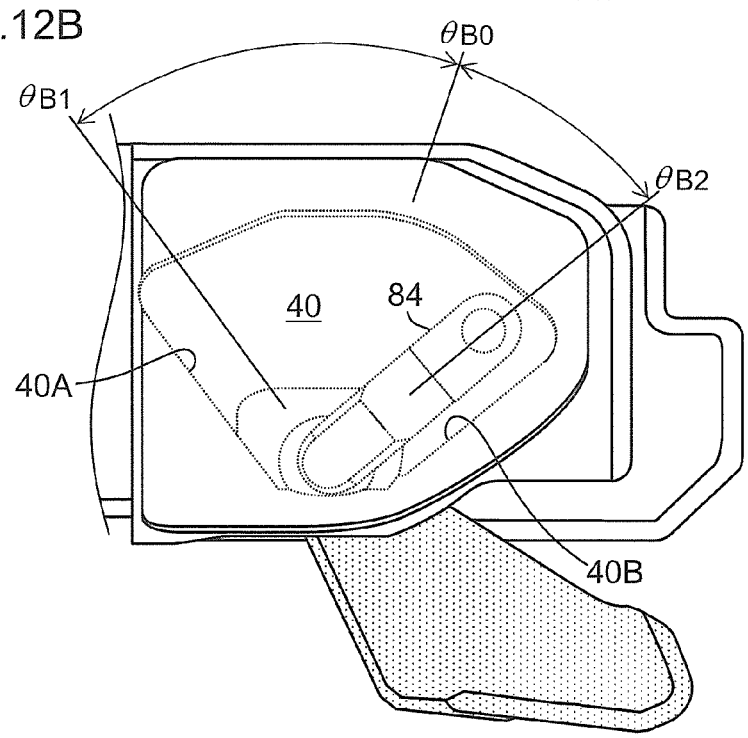
Figure 13A:
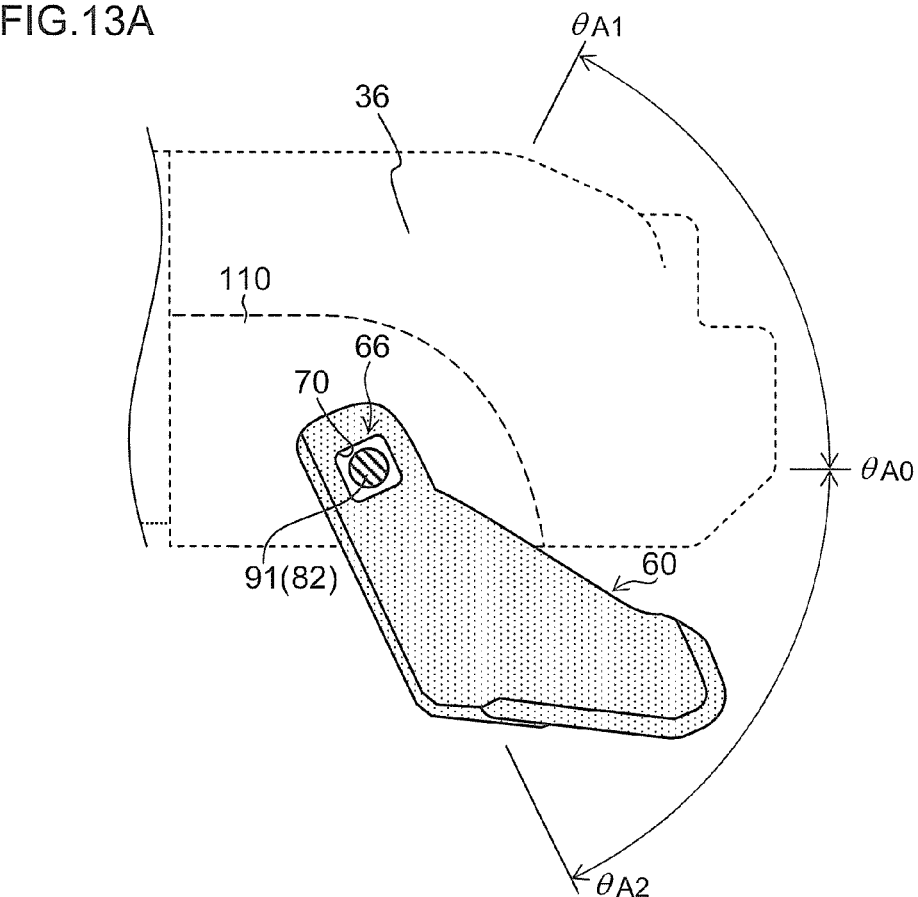
FIGS. 13A and 13B are explanatory drawings used to describe the function of the distal end portion.
Figure 13B:
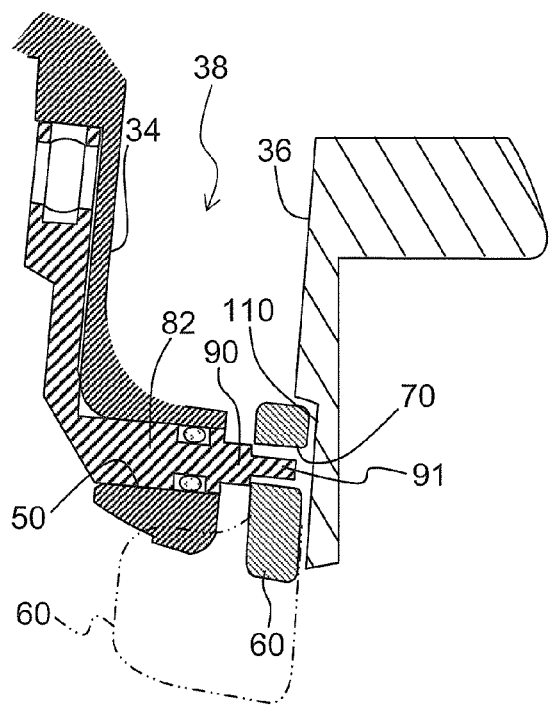

FIGS. 11A, 12A, 13A and 14 are diagrams illustrating the state of the elevator 60 in the elevator housing slit 38 and are diagrams illustrating the rotating shaft 82 (the first shaft portion 90 and the second shaft portion 91), the elevator 60 and the side wall portion 36, and so on, when the side wall portion 36 is seen from a surface which is vertical to the axis of the rotating shaft 82 and which passes through the rotating shaft receiving region 70 of the elevator 60. FIGS. 11B and 12B are diagrams illustrating the state of the erecting lever 84 in the erecting lever housing chamber 40 of the side wall portion 34. Moreover, FIG. 13B is a diagram illustrating the state of FIG. 13A in a cross section vertical to a longitudinal axis that passes through the axis of the rotating shaft 82.

FIGS. 11A and 11B illustrate a state when the cap 26 is attached to the distal end portion 7 and the endoscope 1 is used for operation. When the cap 26 is attached to the distal end portion 7, in the elevator 60, a rotation range toward the reclining side is limited by abutting on the cap 26 so as to limit a rotation range in which at least the elevator 60 is not exposed from the opening portion 38c on the lower surface side of the elevator housing slit 38. Moreover, a rotation range toward the erecting side is limited by abutting on the distal end portion body 30, and so on.

By this means, for example, the rotation range of the elevator 60 which can be operated by the rising operating lever 12 of the operation portion 3 (a rotation angle range around the rotating shaft 82) is limited within the rotation range from θA0 to θA1 as illustrated in FIG. 11A.

Moreover, assuming that the rotation range of the erecting lever 84 at this time (a rotation angle range around the rotating shaft 82) is limited within a rotation range from θB0 to θB1 as illustrated in FIG. 11B, θB0 is on the erecting side with respect to (from) a position in which the erecting lever 84 abuts on a side wall 40B on the reclining side of the erecting lever housing chamber 40. Here, θB1 substantially matches a position when the erecting lever 84 abuts on the side wall portion 40A on the erecting side of the erecting lever housing chamber 40, it is not necessarily limited to this.

Meanwhile, when the distal end portion 7, and so on, is cleaned after the endoscope 1 is used for operation, the cap 26 is detached from the distal end portion 7. By this means, the rotation restriction on the reclining side of the elevator 60 by the cap 26 is released. Further, it becomes possible to rotate the erecting lever 84 up to the position of θB2 on the reclining side from θB0 as illustrated in FIG. 12B, and the rotation range of the elevator 60 which can be operated by the rising operating lever 12 of the operation portion 3 expands to θA2 as illustrated in FIG. 12A.

Further, in a state in which the elevator 60 is set to the reclining side with respect to (from) at least θA0, more preferably, in a state in which the elevator 60 is exposed from the opening portion 38c on the lower surface side of the elevator housing slit 38 to the outside, the elevator 60 is in a position in which it does not overlap the opposing range of a region other than (excluding) the concave portion 110 of the side wall portion 36 at all. At this time, when the elevator 60 is pressed by a finger, a jig, and so on, toward the distal end side of the rotating shaft 82, that is, toward the side wall portion 36, the elevator 60 enters inside the concave portion 110, and the rotating shaft receiving region 70 enters a state in which it is loosely fitted to the second shaft portion 91 in the rotating shaft receiving portion 66 of the elevator 60 as illustrated in FIGS. 13A and 13B. That is, the coupling between the elevator 60 and the rotating shaft 82 is released.

Figure 14:
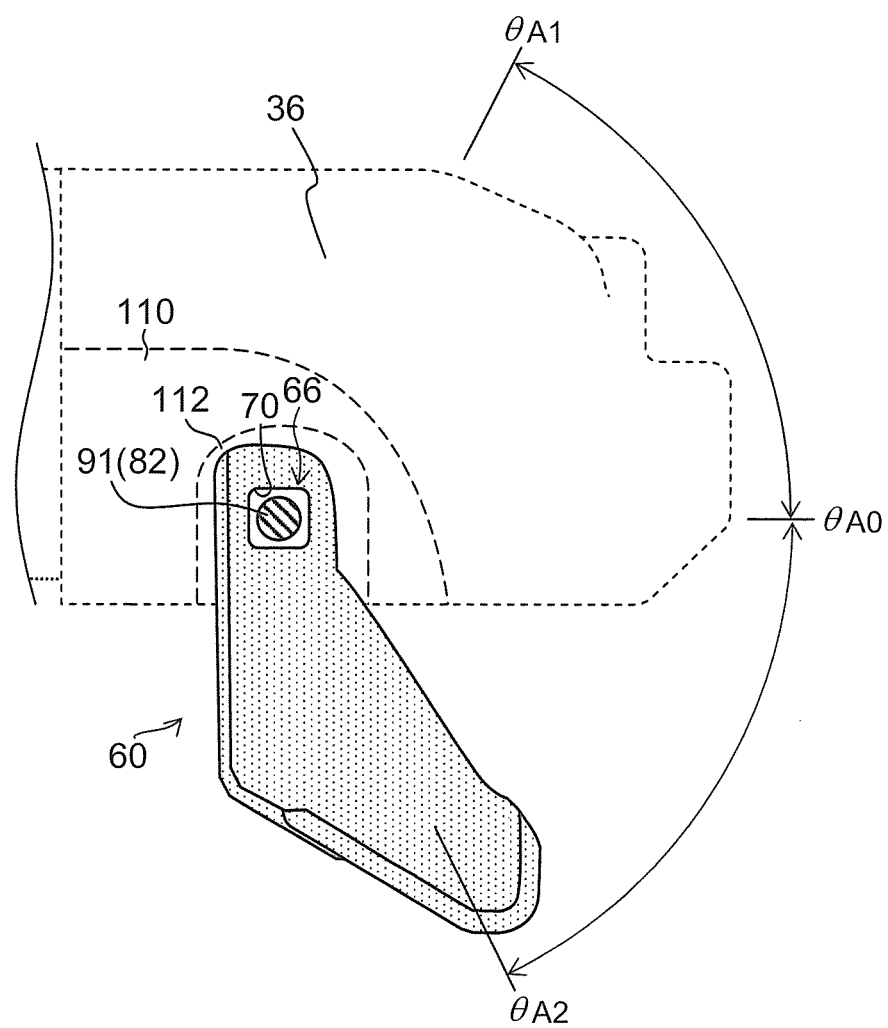
FIG. 14 is an explanatory drawing used to describe the function of the distal end portion.

By this means, it is possible to further rotate the elevator 60 without the rotation of the rotating shaft 82 and the erecting lever 84 within the range of the concave portion 110 and retreat most of the elevator 60 from the elevator housing slit 38 as illustrated in FIG. 14. Therefore, since the gap between the elevator 60 and the wall surface of the elevator housing slit 38 is small and the exposed portion of the wall surface of the elevator housing slit 38 increases, it is possible to clean the elevator 60 and the inside of the elevator housing slit 38 easily and promptly.

Here, like FIGS. 11A, 12B and 13A, the side wall portion 36 functions as a restricting portion which restricts the rotating shaft receiving region 70 of the elevator 60 from moving from a position to engage with the first shaft portion 90 of the rotating shaft 82 to a position to loosely fit the second shaft portion 91, and the elevator 60 is treated as being located in the first position in the rotation direction, when the position of the elevator 60 in the rotation direction is a position on the erecting side with respect to (from) at least θA0, more preferably, a position on the erecting side from a position in which the elevator 60 is exposed from the opening portion 38c on the lower surface side of the elevator housing slit 38 to the outside. Moreover, the side wall portion 36 functions as a restricting portion which allows the rotating shaft receiving region 70 of the elevator 60 to move from the position to engage with the first shaft portion 90 of the rotating shaft 82 to the position to loosely fit the second shaft portion 91, and the elevator 60 is treated as located in the second position in the rotation direction, when it is in a position on the reclining side from at least θA0, more preferably, a position on the reclining side with respect to (from) the position in which the elevator 60 is exposed from the opening portion 38c on the lower surface side of the elevator housing slit 38 to the outside.

Here, the first position can be a position in which the whole of the elevator 60 is housed inside the elevator housing slit 38.

Moreover, the second position can be a position in which at least a part of the elevator 60 is exposed to the outside of the elevator housing slit 38, more preferably, a position in which at least a part of the elevator 60 is exposed from the opening portion 38c on the lower surface side of the elevator housing slit 38 to the outside. In addition, the second position can be a position in which at least a part of the elevator 60 is exposed from the opening portion 38a on the upper surface side of the elevator housing slit 38 to the outside.

Figure 15:
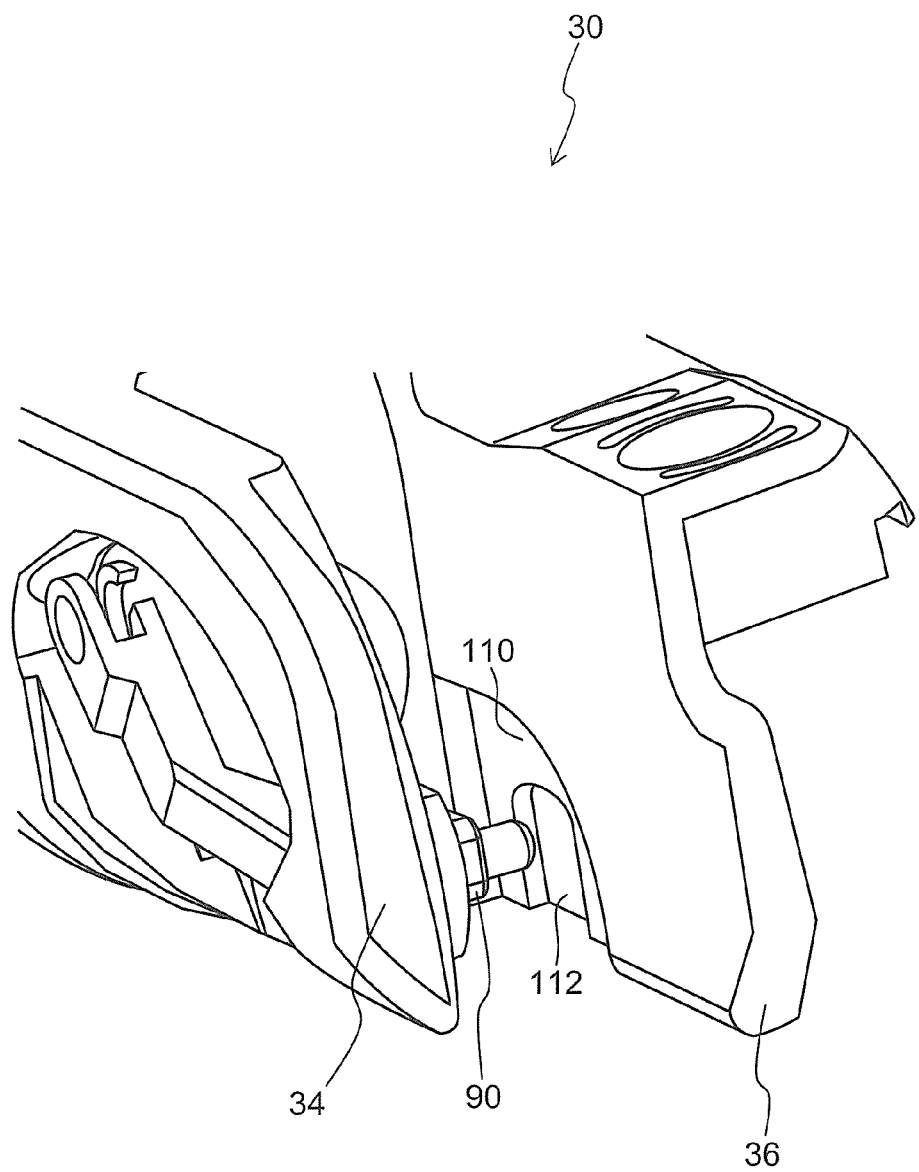
FIG. 15 is a diagram illustrating a concave portion formed in the side wall portion of the distal end portion body.

As above, in the above-mentioned embodiment, for example, as illustrated in FIG. 15, a concave portion 112 which communicates with the lower end from a region opposed to the rotating shaft 82 may be further formed in the side wall portion 36 in the concave portion 110. When the range of that concave portion 112 is shown by the broken line in FIG. 14, after the coupling between the elevator 60 and the rotating shaft 82 is released as mentioned above, it is rotated to an angle at which it overlaps a range in which the concave portion 112 is formed, like the elevator 60 in FIG. 14. Further, by sliding the elevator 60 in the shaft direction of the rotating shaft 82, it is possible to completely detach the elevator 60 from the elevator housing slit 38 through the concave portion 112 and perform cleaning, and so on.

Moreover, in a similar way to the above-mentioned embodiment, when the elevator 60 is in a rotation range on the erecting side with respect to (from) a predetermined angle. For example, the endoscope can be configured so that the coupling between the elevator 60 and the rotating shaft 82 can be released when the elevator 60 is in a rotation range in which the elevator 60 is exposed from the opening portion 38a on the upper surface side of the elevator housing slit 38 to the outside.

What is claimed is:
1. An endoscope comprising:
an insertion portion which includes a distal end and a proximal end;

an operation portion which is provided on a proximal end side of the insertion portion and includes an operating member;

a distal end portion body which is provided on a distal end side of the insertion portion, and has a front surface being a surface in a longitudinal direction of the insertion portion, an upper surface being a surface in a direction in which a treatment tool is led out with respect to the longitudinal direction and a lower surface being a surface on a side opposite to the upper surface with respect to the longitudinal direction;

an elevator which is rotatably provided in the distal end portion body;

a rotating shaft provided with an axis and configured to rotate the elevator around the axis, the rotating shaft including a first shaft portion and a second shaft portion connected with one end of the first shaft portion, wherein a cross section vertical to a direction of the axis of the rotating shaft in the first shaft portion has a non-circular shape, and a cross-sectional area of a cross section vertical to the direction of the axis in the second shaft portion is smaller than a cross-sectional area of the cross section of the first shaft portion;

a rotating shaft receiving portion provided in the elevator, the rotating shaft receiving portion including a rotating shaft receiving region which is engaged with the first shaft portion in a relatively unrotatable manner and is loosely fitted to the second shaft portion in a relatively rotatable manner;

an elevator erecting mechanism configured to rotate the rotating shaft;

an operating wire which includes a proximal-end-side coupling portion coupled with the operating member and a distal-end-side coupling portion coupled with the elevator erecting mechanism, the operating wire being configured to rotate the rotating shaft to recline or erect the elevator when the operating wire is pushed or pulled by operation of the operating member;

an elevator housing slit which is provided in the distal end portion body and forms a space portion to house the elevator, the elevator housing slit including an opening on a side of the upper surface, on a side of the lower surface and on a side of the front surface; and a cap which is detachably provided in the distal end portion body, the cap including an opening window which opens a part of the opening on the side of the upper surface, and a partition wall portion which closes a part of the opening portion on the side of the lower surface in a state in which the cap is attached to the distal end portion body, wherein:

the distal end portion body includes a position restricting portion which is configured to restrict a relative position of the rotating shaft in the direction of the axis with respect to the rotating shaft receiving region of the rotating shaft receiving portion, and a position releasing portion which is configured to release the restriction to the relative position of the rotating shaft in the direction of the axis with respect to the rotating shaft receiving region; and when the elevator is located in a first position in a rotation direction around the rotating shaft, the position restricting portion restricts the relative position of the rotating shaft with respect to the rotating shaft receiving region of the rotating shaft receiving portion to the first shaft portion, and when the cap is detached, the elevator can be moved to a second position in the rotation direction around the rotating shaft, and when the elevator is located in the second position in the rotation direction around the rotating shaft, the elevator is moved into the position releasing portion, and the position releasing portion allows the relative position of the rotating shaft with respect to the rotating shaft receiving region of the rotating shaft receiving portion to move from the first shaft portion to the second shaft portion, when the relative position of the rotating shaft with respect to the rotating shaft receiving region is moved to the second shaft portion, the second shaft portion is loosely fitted to the rotating shaft receiving region in the relatively rotatable manner and the coupling between the rotating shaft and the elevator is released, wherein the position releasing portion is a first concave portion formed in a side wall portion of the distal end portion body, the side wall portion faces a tip end of the rotating shaft, the first concave portion comprises a second concave portion which extends from a position opposed to the tip end of the rotating shaft in the position releasing portion to a lower end of the tip end body portion, and when the elevator is in the second position, the elevator slides in a direction of the axis of the rotating shaft to remove the elevator from the elevator housing slit though the second concave portion.

2. The endoscope according to claim 1, wherein the first position is a position in which a whole of the elevator is housed inside the elevator housing slit.

3. The endoscope according to claim 1, wherein the second position is a position in which at least a part of the elevator is exposed to outside of the elevator housing slit.

4. The endoscope according to claim 3, wherein the second position is a position in which at least a part of the elevator is exposed from the part of the opening on the side of the lower surface to outside.

5. The endoscope according to claim 3, wherein the second position is a position in which at least a part of the elevator is exposed from the part of the opening on the side of the upper surface to outside.

6. The endoscope according to claim 1, wherein the rotating shaft is configured in a cantilever shape in which one end of the rotating shaft is a fixed end fixed to the elevator erecting mechanism and another end is a free end.

7. The endoscope according to claim 1, wherein:
the elevator erecting mechanism includes an elevator erecting lever coupled with the rotating shaft;
the distal-end-side coupling portion of the operating wire is coupled with the elevator erecting lever; and
when the operating wire is pushed or pulled by operation of the operating member, the operating wire rotates the rotating shaft through the elevator erecting lever to recline or erect the elevator.

* * * * *